United States Patent
Binder (10) Patent No.: US 6,468,211 B1
(45) Date of Patent: Oct. 22, 2002

(54) CARDIOPULMONARY EXERCISE TESTING APPARATUS AND METHOD

(75) Inventor: Andrew S. Binder, Santa Barbara, CA (US)

(73) Assignee: Orca Diagnostics Corporation, Santa Barbara, CA (US)

(*) Notice: Subject to any disclaimer, the term of this patent is extended or adjusted under 35 U.S.C. 154(b) by 0 days.

(21) Appl. No.: 09/686,315

(22) Filed: Oct. 10, 2000

Related U.S. Application Data (62) Division of application No. 09/322,320, filed on May 28, 1999.

(51) Int. Cl.[7] ............................................. A61B 5/00
(52) U.S. Cl. .................... 600/301; 600/520; 600/483; 482/7
(58) Field of Search ................................. 600/300, 301, 600/483, 500, 520; 482/8

(56) References Cited

U.S. PATENT DOCUMENTS

| | | | |
|---|---|---|---|
| 4,368,740 A | 1/1983 | Binder | 128/718 |
| 5,435,315 A | * 7/1995 | McPhee et al. | 600/483 |
| 5,462,504 A | * 10/1995 | Trulaske et al. | 482/8 |
| 5,474,090 A | * 12/1995 | Begun et al. | 600/520 |

OTHER PUBLICATIONS

Sue, D.Y.; Wasserman, K.; "Impact of integrative cardiopulmonary exercise testing on clinical decision making," *Chest* 99:981–92 (1991).

Beaver, W.L.; Wasserman, K.; Whipp, B.J.; "A new method for detecting anaerobic threshold by gas exchange," *J. Appl. Physiol.* 60:2020–2027 (1986).

Weber, K.T.; Janicki, J.S.; McElroy, P.A.; "Determination of aerobic capacity and the severity of chronic cardiac and circulatory failure," *Circulation* 76(suppl. VI):40–45 (1987).

Noguchi, H; Ogushi, Y; et. al.; "Breath by breath VCO2 and VO2 require compensation for transport delay and dynamic response," *J. Appl. Physiol.* 52:79–84 (1982).

\* cited by examiner

*Primary Examiner*—Robert L. Nasser
(74) *Attorney, Agent, or Firm*—Lyon & Lyon LLP (57) ABSTRACT

A gas analysis apparatus, and a method for calibrating it and for compensating measurement errors, are disclosed. This method and apparatus are particularly suited for use during a cardipulmonary exercise test by a test subject. The oxygen and carbon dioxide concentrations of the subject's breath are measured, and errors are compensated based on the results of previous calibration. These compensated measurements, as well as other physiological data monitored during the cardiopulmonary exercise test quantities calculated from these measurements, are presented as a series of graphs in a logical order to enhance their diagnostic and prognostic value. A facemask and headstraps are adapted for use with the gas analysis apparatus. The facemask possesses a plurality of pins fitting into corresponding holes in the headstraps, and the headstraps possess quick-release attachment means to provide for quickly securing the face mask to or removing it from a subject.

11 Claims, 6 Drawing Sheets

CARDIOPULMONARY EXERCISE TESTING APPARATUS AND METHOD

This is a divisional patent application of co-pending patent application Ser. No. 09/322,320 filed May 28, 1999.

BACKGROUND OF THE INVENTION

The field of invention is cardiopulmonary exercise testing.

Exercise capacity is the best predictor of the future health of patients who suffer coronary artery disease or who have suffered heart failure. These diseases are the leading causes of hospitalization and mortality in the United States. Thus, exercise testing is a basic tool of clinicians, and is widely used. Analysis of expired gas during exercise is commonly known as cardiopulmonary exercise testing ("CPX") or metabolic exercise testing, and is often referred to as exercise testing with gas analysis. CPX has been considered by many clinicians to be difficult and expensive to perform, and because of this many clinicians have foregone CPX in favor of less accurate tests that merely estimate the measurements made directly by CPX. Such tests typically require the patient to exercise under steady state conditions—that is, a constant work level—for a fixed period of time, at the end of which the patient's heart rate, breathing rate, and oxygen consumption ideally plateau out to constant levels. The constant work level is then increased to a higher constant work level for a fixed time, and the patient's measurements are again expected to plateau out at the end of that time. This process may be repeated several times.

The measurement $\dot{V}O_2$ is the patient's oxygen uptake; that is, the rate of oxygen consumption by a patient during an exercise test. This measurement is sometimes referred to in terms of Mets, which are multiples of resting $\dot{V}O_2$, assumed to be 3.5 milliliters per kilogram per minute. Peak $\dot{V}O_2$, which is the maximum rate of oxygen consumption by a patient during an exercise test, is a good objective measurement of a patient's aerobic exercise capacity, and usually reflects cardiac function. As commonly performed, exercise testing merely estimates peak $\dot{V}O_2$ from exercise duration on a treadmill, workload on a stationary bicycle or distance walked. Such estimates may be substantially influenced by factors other than the patient's medical condition, however, such as the degree of patient effort and motivation, the degree of patient familiarity with the test equipment (sometimes referred to as the training effect); the disparity between expected oxygen requirements and actual oxygen uptake widens as heart disease worsens. This gap is filled by anaerobic processes, which result in the production of lactic acid when carbohydrate is metabolized in the absence of oxygen uptake. This leads to errors when $\dot{V}O_2$ is estimated by assuming the whole exercise process is fueled by aerobic metabolism.

$\dot{V}CO_2$ is the rate of carbon dioxide production by a patient during exercise. $\dot{V}CO_2$ relative to $\dot{V}O_2$ is influenced by which substrate is metabolized (fat vs. carbohydrate) and whether anaerobic processes and lactic acid production occur. Therefore, $\dot{V}CO_2$ cannot be estimated. $\dot{V}E$ (minute ventilation) is the volume of air breathed per minute by a patient, which varies proportionally to $\dot{V}CO_2$. $\dot{V}CO_2$ relative to $\dot{V}E$ is influenced by the presence of heart or lung disease. The calculation of $\dot{V}O_2$ and $\dot{V}CO_2$ by numerical integration of the product of expiratory airflow with $O_2$ and $CO_2$ concentrations over the duration of a breath is taught in the prior art.

Two different sources of error are commonly found in gas analysis equipment: delay time and response time. Delay time is the time taken for the physical transport of a gas sample from the mouth to the gas analyzers. On the other hand, response time, also known as rise time, is intrinsic to a gas analyzer. Response time is the time that elapses between exposure of a gas sample to a gas analyzer and an output signal from the gas analyzer achieving 67% of the full-scale signal that would correspond to the actual concentration of the gas. For example, if a gas sample containing carbon dioxide at a 10% concentration were exposed to a gas analyzer, the response time of that gas analyzer would be the time taken for that gas analyzer to output a signal indicating a 6.7% concentration of carbon dioxide. The errors introduced by the delay time and the response time prevent the accurate time synchronization of $O_2$ and $CO_2$ signals with separately-measured flow signals that do not experience delay time and response time errors, and thus prevent realtime measurement of $\dot{V}O_2$ and $\dot{V}CO_2$ and realtime calculation of derived parameters that depend on $\dot{V}O_2$ and $\dot{V}CO_2$, such as $\dot{V}E/\dot{V}O_2$ and $\dot{V}E/\dot{V}CO_2$.

Before calibrating a CPX system, it is often desirable to purge it of remnants of test gas or previous reference gas and ensure that ambient air is present in the system. This is essential for calibration, because if the system is not filled with ambient air before calibration, it will not be at a standard baseline state for the initiation of calibration.

Masks for collecting gas during exercise testing are known in the art, and may be used instead of the traditional mouthpiece and noseclip. However, tradeoffs are made between patient comfort during use, ease with which the operator can place the mask on the patient, and security of attachment to the patient. Typically masks which securely attach to the patient during exercise are difficult to put on the patient, and are uncomfortable; such discomfort can distract the patient during CPX and result in submaximal effort, or in early test termination due to patient discomfort.

SUMMARY OF THE INVENTION

The present invention is directed toward a method and apparatus for cardiopulmonary exercise testing.

In a first, separate aspect of the invention, a simulated breath, composed of a known volume of calibration gas containing known concentrations of oxygen, carbon dioxide and nitrogen approximating those of exhaled air, is released within a cardiopulmonary exercise testing apparatus at a flow rate and pressure profile similar to an exhaled breath. The cardiopulmonary exercise testing apparatus measures the flow rate and composition of this gas. Those measurements serve as input for a software program that calculates the necessary compensation and calibration factors for gas sensor delay time, gas sensor response time, gas sensor zero offset, gas sensor span adjustment, and flow sensor calibration. The software program uses these compensation and calibration factors to co-align the gas concentration measurement signals and the flow rate signals such that integration of flow and gas concentration signals can be accomplished breath by breath during exercise testing.

In a second, separate aspect of the invention, measurements of $\dot{V}O_2$ and $\dot{V}CO_2$, exhaled breath flow rate ($\dot{V}E$), heart rate, and oxygen saturation, as well as derived factors of diagnostic importance, are displayed in a series of four charts that organize and present this information for ease of use and interpretation to facilitate diagnosis.

In a third, separate aspect of the invention, a single pump is used to both purge the cardiopulmonary exercise test apparatus of calibration gas before calibration or testing and to draw the sample gas through the gas analyzers during the calibration procedure or patient testing.

In a fourth, separate aspect of the invention, a face mask used to collect a patient's exhaled breath possesses a plurality of pins. Each headstrap contains a hole corresponding to a headstrap pin, and is attached to the face mask by placing the hole over the corresponding headstrap pin. Each headstrap can be adjusted and secured in a single step, and quickly and easily removed from its corresponding headstrap pin.

DETAILED DESCRIPTION OF THE PREFERRED EMBODIMENTS

Detection and analysis of human respiratory gas exchange during exercise, especially when combined with pulse rate and blood oxygen saturation data, provide important diagnostic information. Exercise requires the integrated responses of the cardiovascular, pulmonary, and musculoskeletal systems, which together reflect a patient's overall health. These exercise responses provide a functional assessment of the cardiovascular, pulmonary and metabolic systems which cannot be achieved by any test performed while the patient is at rest.

The present invention is designed to sense, analyze and display cardiopulmonary data gathered breath by breath during an exercise test. One breath is preferably defined as the interval between two successive inspiratory efforts. The measurements collected breath-by-breath during the exercise test include, but are not limited to, oxygen concentration and carbon dioxide concentration in expiratory air, inspiratory and expiratory airflow, heart rate, respiratory rate, and percent blood oxygen saturation.

Figure 1:
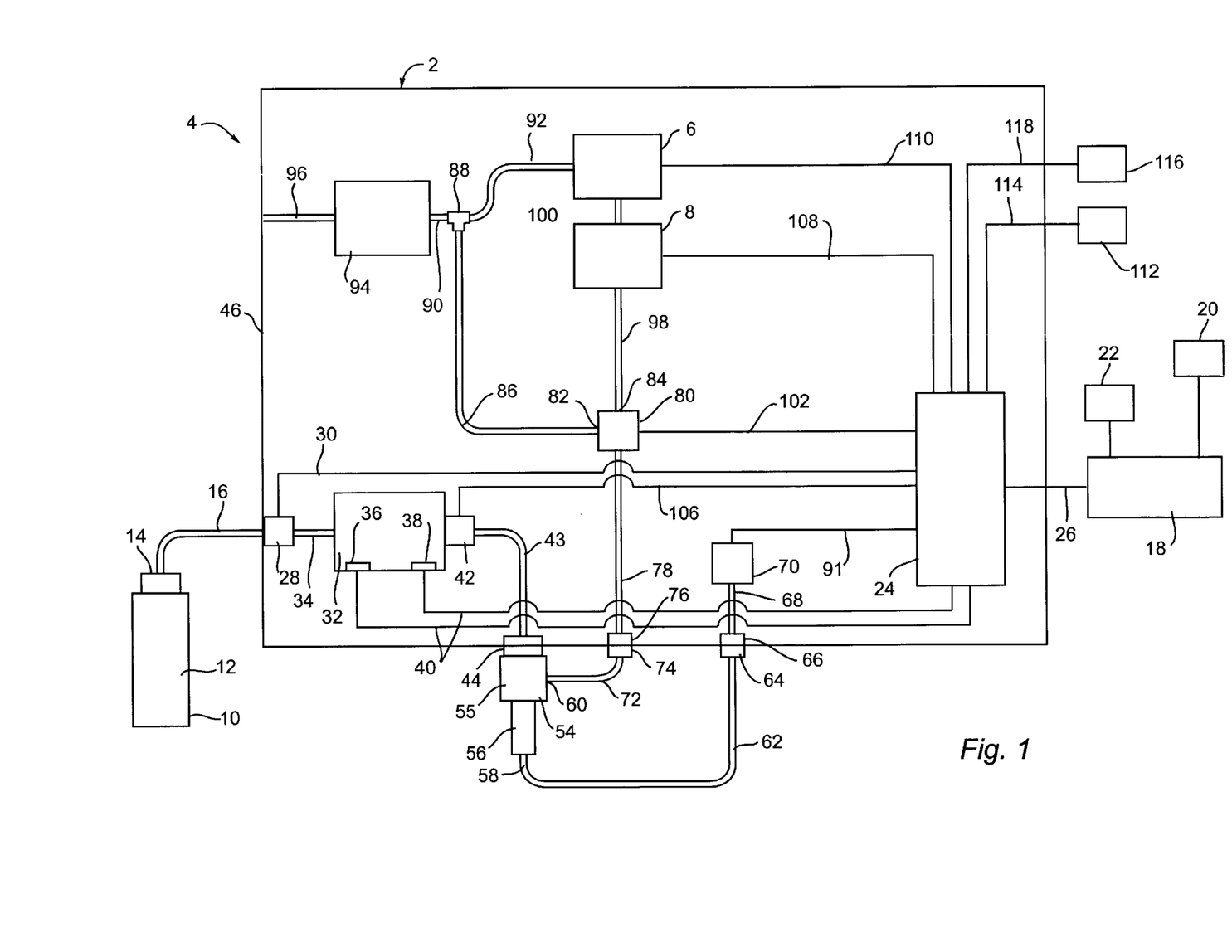
FIG. 1 is a schematic view of an exercise test apparatus, configured for calibration.

Before the exercise test begins, a test station 2 is preferably calibrated or verified. The test station 2 is part of an exercise test apparatus 4.

Calibration

The objective of calibration is to zero and scale an oxygen analyzer 6 and a carbon dioxide analyzer 8, determine the transit delay time for a gas sample to travel from the patient's mouth to the oxygen analyzer 6 and the carbon dioxide analyzer 8, and determine the response time (also known as rise time) of the oxygen analyzer 6 and the carbon dioxide analyzer 8. The physical length and diameter of the gas sample tubing, and the pump flow which draws the gas sample, influence the delay time and rise time.

Referring to FIG. 1, a schematic view of the test station 2, as configured for calibration, is shown. A container 10 containing calibration gas 12 of known composition is located adjacent to the test station 2. Preferably, the calibration gas 12 is a mixture of substantially 16% oxygen, substantially 4% carbon dioxide, and substantially 80% nitrogen, because this mixture of gases approximates the gas content of normal human exhaled breath. However, the calibration gas 12 may comprise any mixture of gases in any proportion as long as oxygen and carbon dioxide gases are part of the calibration gas 12, and as long as the composition of the calibration gas 12 is known in advance of calibration. A pressure regulator 14 is attached to the container 10. Preferably, the pressure regulator 14 is preset and nonadjustable so that calibration gas 12 is supplied to the test station 2 at a relatively consistent pressure. The pressure regulator 14 is in turn connected to one end of a calibration gas inlet hose 16, the other end of which is attached to an inlet valve 28 connected to the test station 2. The inlet valve 28 is connected to one end of an inlet connection line 34, the other end of which is connected to a compression bottle 32.

A computer 18 is a part of the exercise test apparatus 4, and is attached to the test station 2. The user of the test station 2 may advantageously attach the test station 2 to an existing computer 18 that it already owns, in order to reduce costs. Optionally, however, the computer 18 may be included within the test station 2. The computer 18 is preferably electronically connected to a display 20 and a printer 22. The display 20 may be, for example, a monitor or a liquid crystal display.

The test station 2 includes an analog-to-digital ("A/D") converter 24 that converts analog signals from various sensors associated with the test station 2 into digital signals for transmission to the computer 18, and that converts digital control signals from the computer 18 into analog signals transmitted to various actuators associated with the test station 2. Preferably, the A/D converter 24 and the computer 18 are interconnected via an external communications cable 26. The computer 18 preferably stores all sensor data transmitted to it until commanded by an operator to delete it.

The operator initiates calibration via the computer 18. The computer 18 transmits a command to the test station 2 to open the inlet valve 28 and close the outlet valve 42. Optionally, the inlet valve 28 is directly connected to the compression bottle 32, and no inlet connection line 34 is used. This command is transmitted through the external communications cable 26 to the A/D converter 24, which translates the command into analog form and sends a signal through a valve command wire 30 to the inlet valve 28, commanding the inlet valve 28 to open. Calibration gas 12 from the container 10 then enters the test station 2 through the pressure regulator 14, the calibration gas inlet hose 16 and the inlet valve 28. The inlet valve 28 is preferably connected to a compression bottle 32 by an inlet connection line 34. Optionally, the inlet valve 28 may be attached directly to the compression bottle 32, thereby eliminating the inlet connection line 34. The compression bottle 32 is filled to a known pressure, which is measured by a pressure sensor 36 located within the compression bottle 32. The temperature of the calibration gas within the compression bottle 32 is measured by a temperature sensor 38 located within the compression bottle 32. Measurements from the pressure sensor 36 and the temperature sensor 38 are transmitted through sensor wires 40 to the A/D converter 24, which in turn transmits those measurements to the computer 18. Because the volume of the compression bottle 32 is known, and the pressure sensor 36 and the temperature sensor 38 measure the final pressure and temperature of the calibration gas 12 within the compression bottle 32, the compressed volume of the gas within the compression bottle 32 can be calculated by the computer 18. Preferably, the compressed volume of calibration gas 12 within the compression bottle ranges from 0.5–1.0 liters; however, any volume may be used as long as its amount is accurately known or measured.

An outlet valve 42 is attached to the compression bottle 32. An outlet valve hose 43 is attached at one end to the outlet valve 42, and at its other end to a calibration port 44. The length and volume of the outlet valve hose 43 is preferably kept as small as possible, in order to minimize dead space. The calibration port 44 is attached to a shell 46 of the test station 2. The shell 46 is simply the enclosure which preferably defines the outer surface of the test station 2. While the test station 2 may be open to the environment, it is preferable to enclose it for safety, durability, and attractiveness, among other reasons.

The calibration port 44 is preferably shaped to provide for a pressure fit with an adapter 54. The adapter 54 is attached to and in flow communication with a flow sensor 56. The adapter 54 also possesses a gas analysis outlet port 60. Preferably, the flow sensor 56 is a pneumotachograph constructed as taught by U.S. Pat. No. 4,905,709, which is hereby incorporated by reference. However, any other type of accurate flow sensor may be used to measure flow rate, if desired. Preferably, the flow sensor 56 is connected to the adapter 54 in such a manner as to enable the flow sensor 56 to be easily attached to and removed from the adapter 54, but to keep it securely fastened to the adapter 54 during calibration and exercise testing, such as by a pressure fit. The flow sensor 56 possesses a flow sensor outlet port 58.

A flow sensor outlet hose 62 is attached at one end to the flow sensor outlet port 58 on the flow sensor 56, and at the other end to a first flow sensor outlet hose connector 64. The first flow sensor outlet hose connector 64 mates with a second flow sensor outlet hose connector 66, which is preferably attached to the shell 46 of the test station 2. The first flow sensor outlet hose connector 64 and the second flow sensor outlet hose connector 66 may be any connectors that enable convenient connection and disconnection from one another but have low dead space to prevent expansion and mixing. A pressure transducer hose 68 is located within the test station 2, and is connected at one end to the second flow sensor outlet hose connector 66 and at the other end to a pressure transducer 70. Preferably, the pressure transducer 70 is a differential pressure transducer possessing a port open to ambient air, and compares the pressure of the ambient air to the pressure of the gas transmitted to it through the pressure transducer hose 68.

A sampling hose 72 is attached at one end to the gas analysis outlet port 60 on the adapter 54 and at the other end to a first gas analysis outlet hose connector 74. The first gas analysis outlet hose connector 74 mates with a second gas analysis outlet hose connector 16, which is preferably attached to the shell 46 of the test station 2. The first gas analysis outlet hose connector 74 and the second gas analysis outlet hose connector 76 may be any connectors that enables convenient connection and disconnection from one another but have low dead space to prevent expansion and mixing. An internal gas transfer hose 78 is located within the test station 2, and is connected at one end to the second gas analysis outlet hose connector 76 and at the other end to a purge valve 80. The purge valve 80 is located within the test station 2, and is capable of accepting gas flow from the internal gas transfer hose 78 and switching that gas flow to one of two outlets attached to it.

One outlet of the purge valve 80 is a purge outlet 82, and the other outlet of the purge valve 80 is a gas analysis outlet 84. Preferably, a purge valve outlet hose 86 is attached at one end to the purge valve 80 and at the other end to a T-connector 88. Preferably, the first T-connector 88 is further attached to a pump inlet hose 90 and to a gas analyzer outlet hose 92. The pump inlet hose 90 is connected at one end to the T-connector 88 and at the other end to a pump 94. A pump outlet hose 96 is connected at one end to the pump 94, and at the other end to the shell 46 of the test station 2 such that the pump outlet hose 96 vents outside the test station 2.

Several variations of the connections disclosed above will be apparent to those skilled in the art For example, the pump 94 may optionally be placed adjacent to the shell of the test station 2 such that it vents directly outside the test station 2, eliminating the need for the pump outlet hose 96. The first T-connector 88 can optionally be connected directly to the pump 94, eliminating the pump inlet hose 90. Alternately, the purge valve outlet hose 86, the gas analyzer outlet hose 92, and the pump inlet hose 90 may be interconnected by methods or mechanisms other than the T-connector 88, although the T-connector 88 is preferred due to its low cost, ease of use, and positive contribution to maintainability.

One end of a gas analysis inlet hose 98 is attached to the gas analysis outlet 84 of the purge valve 80, and the other end is connected to the carbon dioxide analyzer 8. The carbon dioxide analyzer 8 is connected to the oxygen analyzer 6 by an analyzer connector hose 100. One end of the gas analyzer outlet hose 92 is connected to the oxygen analyzer 6, and the other end is connected to the T-connector 88. The oxygen analyzer 6 is preferably connected to the carbon dioxide analyzer 8 in series in this order. The oxygen analyzer 6 typically offers some resistance to gas flow through it, and thereby results in downstream mixing of gases from discrete breaths that have passed through it. However, in the preferred embodiment, the carbon dioxide analyzer 8 has low resistance and substantially no mixing of gas within. Thus, if the oxygen analyzer 6 offers such resistance or causes downstream mixing of gases from discrete breaths, the carbon dioxide analyzer 8 is preferably placed first in a series arrangement Otherwise, the gases passed on from the oxygen analyzer 6 can be mixed, negating the breath-by-breath analysis desired from the exercise test apparatus 4. Optionally, the oxygen analyzer 6 and the carbon dioxide analyzer 8 may be arranged in parallel, for example, by having the gas analysis inlet hose 98 branch to both analyzers. Such a parallel arrangement, however, requires additional pneumatic hoses, adding to cost, complexity, and size.

While the compression bottle 32 is being filled, the test station 2 is purged. The computer 18 transmits a command to the purge valve 80 to close the gas analysis outlet 84 and open the purge outlet 82. This command is transmitted through the external communications cable 26 to the A/D converter 24, which translates the command into analog form and sends a signal through a purge valve command wire 102 to the purge valve 80. The pump 94 is activated automatically when power is applied to the test station 2, and remains on as long as the test station 2 is on. The pump 94 thus draws in ambient air through the flow sensor 56, pulling it through the adapter 54, the sampling hose 72, the internal gas transfer hose 78, the purge valve 58, the purge valve outlet hose 86, the T-connector 88, and the pump inlet hose 90, into the pump then expelling that ambient air from the test station 2 through the pump outlet hose 72. The pump thereby purges those components with ambient air.

Purging continues for a preset duration that is sufficient to allow for the complete filling of the compression bottle 32 and for complete purging. This purging duration is a function of the flow rate generated by the pump 94, the preset pressure regulator 14, and the volume of the components of the test station 2 that are purged. The preset purging duration is stored in the computer 18. After the preset purging duration is complete, the computer 18 issues a command to the purge valve to close the purge outlet 82 and open the gas analysis outlet 84. This command is transmitted through the external communications cable 26 to the A/D converter 24, which translates the command into analog form and sends a signal through the purge valve command wire 102 to the purge valve 80. The pump 94 remains on. An additional time period, preferably five seconds, is allowed for the carbon dioxide analyzer 8 and the oxygen analyzer 6 to measure and record the concentrations of $CO_2$ and $O_2$ in the ambient air drawn into the carbon dioxide analyzer 8 and the oxygen analyzer 6 during purging. During the last second of that five-second period, the gas concentration transitions caused by purging are typically substantially complete, and the gas concentrations reach a substantially constant plateau. The concentration of $O_2$ and $CO_2$ in ambient air is known. Thus, the output signals from the carbon dioxide analyzer 8 and the oxygen analyzer 6, corresponding to the measured amounts of $CO_2$ and $O_2$, respectively, serve as the baseline signals for establishing the scaling factors and offsets for each analyzer. The analog output signals from the oxygen analyzer 6 and the carbon dioxide analyzer 8 are preferably voltages, the level of which corresponds to a given gas concentration. The output signals from the oxygen analyzer 6 travel through an oxygen analyzer wire 110 to the A/D converter 24, where they are converted into digital form and transmitted through the external communications cable 26 to the computer 18. The signal output from the oxygen analyzer 6 for this is five-second time period is stored by the computer 18, and the plateau value over the last second of that time period is averaged over that one-second time to generate the constant SignalBO2. SignalBO2 is stored in the computer 18. Similarly, the output signals from the carbon dioxide analyzer 8 travel through a carbon dioxide analyzer wire 108 to the A/D converter 24, where they are converted into digital form and transmitted through the external communications cable 26 to the computer 18. The signal output from the carbon dioxide analyzer 8 for this five-second time period is stored by the computer 18, and the plateau value over the last second of that time period is averaged over that one-second time to generate the constant SignalBCO2. SignalBCO2 is stored in the computer 18. More or less time than five seconds may be allotted for these measurements, if desired; however, five seconds is generally more than enough time to allow the gas concentrations to stabilize and to calculate SignalBO2 and SignalBCO2.

The computer 18 then issues a command to the outlet valve 42 to open. This command is transmitted through the external communications cable 26 to the A/D converter 24, which translates the command into analog form and sends a signal through an outlet valve command wire 106 to the outlet valve 42. The outlet valve 42 is opened far enough in a short enough time to release the calibration gas 12 from the compression bottle 32 at a flow rate and pressure, over the duration of calibration gas 12 outflow from the compression bottle 32, that are similar to that of an exhaled breath. Indeed, the outflow of calibration gas 12 from the compression bottle 32 may be accompanied by a whooshing sound approximating the sound made by a person exhaling after a deep breath.

When the outlet valve 42 opens, the pressurized calibration gas 12 within the compression bottle 32 rushes out through the outlet valve 42, passing through the outlet valve hose 43, the calibration port 44, and the adapter 54. A portion of the calibration gas 12 entering the adapter 54 is drawn off from the adapter 54 through the gas analysis outlet port 60, due to the suction of the pump 94 which is in flow communication with the gas analysis outlet port 60. A portion of the calibration gas 12 thus travels through the sampling hose 72, the first gas analysis outlet hose connector 74, the internal gas transfer hose 78, the purge valve 80, and the gas analysis inlet hose 98 to the carbon dioxide analyzer 8. The carbon dioxide analyzer 8 measures the amount of $CO_2$ in the calibration gas 12, and transmits that analog measurement to the A/D converter 24 through the carbon dioxide analyzer wire 108. The A/D converter 24 converts that analog signal to a digital signal and transmits it to the computer 18 via the external communications cable 26.

The calibration gas 12 then flows from the carbon dioxide analyzer 8 to the oxygen analyzer 6 via the analyzer connector hose 100. The oxygen analyzer 6 measures the amount of $O_2$ in the calibration gas 12, and transmits that analog measurement to the A/D converter 24 through the oxygen analyzer wire 110. The A/D converter 24 converts that analog signal to a digital signal and transmits it to the computer 18 via the external communications cable 26.

The calibration gas 12 within the oxygen analyzer 6 is then drawn through the gas analyzer outlet hose 92, the T-connector 88, and the pump inlet hose 90 into the pump 94, where it is then expelled from the test station 2 through the pump outlet hose 96.

The flow sensor 56 attached to the adapter 54 is in flow communication with the pressure transducer 70 via the flow sensor outlet port 58, the flow sensor outlet hose 62 and the pressure transducer hose 68. Measurements from the pressure transducer 70 are transmitted to the A/D converter 24 through the pressure transducer signal wire 91. The A/D converter 24 converts that analog signal to a digital signal and transmits it to the computer 18 via the external communications cable 26. The computer 18 then converts the pressure measurement into a flow measurement; the flow rate of the calibration gas 12 is proportional to the difference in pressure between the pressure measured by the pressure transducer 70 and the pressure of the ambient air. The computer 18 then determines the volume of the flow through the flow sensor 56 by integrating the flow rate with respect to time.

The calibration process continues for an additional period of time after the pressure within the compression bottle 32 has reached substantial equilibrium with ambient pressure. Preferably, this additional time period is five seconds. At that time, flow essentially ceases and the gas concentration measurements from the carbon dioxide analyzer 8 and the oxygen analyzer 6 reach substantial equilibrium. During the last second of this period, delay time and rise time notwithstanding, the carbon dioxide analyzer 8 and the oxygen analyzer 6 have typically achieved substantially full response and are substantially accurately sensing the known concentrations of the $CO_2$ and $O_2$, respectively, within the calibration gas 12. During this time period, the oxygen analyzer 6 and the carbon dioxide analyzer 8 measure and record the concentrations of $O_2$ and $CO_2$ within the calibration gas 12. The concentrations of $O_2$ and $CO_2$ within the calibration gas 12 are known. Thus, the output signals from the oxygen analyzer 6 and the carbon dioxide analyzer 8, corresponding to the measured amounts of $O_2$ and $CO_2$, respectively, serve as the response signals for establishing the scaling factors and offsets for each analyzer. The output signals from the oxygen analyzer 6 travel through an oxygen analyzer wire 110 to the A/D converter 24, where they are converted to digital form and transmitted through the external communications cable 26 to the computer 18. The signal output from the oxygen analyzer 6 for this five-second time period is stored by the computer 18, and the plateau value over the last second of that time period is averaged over that one-second time to generate the constant SignalAO2. SignalAO2 is stored in the computer 18. Similarly, the output signals from the carbon dioxide analyzer 8 travel through an carbon dioxide analyzer wire 108 to the A/D converter 24, where they are converted to digital form and transmitted through the external communications cable 26 to the computer 18. The signal output from the carbon dioxide analyzer 8 for this five-second time period is stored by the computer 18, and the plateau value over the last second of that time period is averaged over that one-second time to generate the constant SignalACO2. SignalACO2 is stored in the computer 18. More or less time than five seconds may be allotted for these measurements, if desired; however, five seconds is generally more than enough time to allow for stable measurement and calculation of Signal AO2 and Signal ACO2.

Preferably, the calibration factors are calculated according to a simple linear information. The oxygen calibration factors are calculated by the computer 18 according to the following equations:

$$SlopeO2=(RefO2-BaselineO2)/(SignalAO2-SignalBO2) \quad (1)$$

$$OffsetO2=BaselineO2-SlopeO2*SignalBO2=RefO2-Slope*SignalAO2 \quad (2)$$

where:

RefO2 is the known concentration of oxygen within the calibration gas 12, which in the preferred embodiment is 16% $O_2$.

BaselineO2 is the known concentration of oxygen present in ambient air, which is 20.93% $O_2$.

SignalAO2, as described above, is the average steady-state percentage of oxygen in the calibration gas 12 measured as present in the oxygen analyzer 6 for a time period at the end of calibration.

SignalBO2, as described above, is the average steady-state percentage of oxygen in the ambient air measured as present in the oxygen analyzer 6 for a time period at the end of purging.

Thus, because RefA and Baseline are known, and SignalAO2 and SignalBO2 have been calculated by the computer 18, SlopeO2 and OffsetO2 may be easily calculated.

Similarly, the carbon dioxide calibration factors is calculated by the computer 18 according to the following equations:

$$SlopeCO2=(RefCO2-BaselineCO2)/(SignalACO2-SignalBCO2) \quad (3)$$

$$OffsetCO2=BaselineCO2-SlopeCO2*SignalBCO2=RefCO2-SlopeCO2*SignalACO2 \quad (4)$$

where:

RefCO2 is the known concentration of carbon dioxide gas within the calibration gas 12, which in the preferred embodiment is 4% $CO_2$.

BaselineCO2 is the known concentration of carbon dioxide gas present in ambient air, which is 0.03% $CO_2$.

SignalACO2, as described above, is the average steady-state percentage of carbon dioxide in the calibration gas 12 measured as present in the carbon dioxide analyzer 8 for a time period at the end of calibration.

SignalBCO2, as described above, is the average steady-state percentage of carbon dioxide in the ambient air measured as present in the carbon dioxide analyzer 8 for a time period at the end of purging.

The quantities SlopeO2 and SlopeCO2 correspond to the span associated with the oxygen analyzer 6 and the carbon dioxide analyzer 8, respectively. Similarly, the quantities OffsetO2 and OffsetCO2 correspond to the offset of the oxygen analyzer 6 and the carbon dioxide analyzer 8, respectively.

Optionally, other curve fitting techniques may be used to determine the slope and the offset, if desired, for both $O_2$ and $CO_2$, especially if the oxygen analyzer 6 or the carbon dioxide analyzer 8, or both, are nonlinear.

The quantities calculated in Equations (1), (2), (3), and (4) above-SlopeO2, OffsetO2, SlopeCO2, and OffsetCO2—are then used to compensate for gas sensor span and offset, using the following equations:

$$C_{measured}O2(t)=C_{signal}O2(t)*SlopeO2+OffsetO2 \quad (5)$$

$$C_{measured}CO2(t)=C_{signal}CO2(t)*SlopeCO2+OffsetCO2, \quad (6)$$

where $C_{measured}O2(t)$ is the oxygen concentration sensed at time t by the oxygen analyzer after correction for span and offset;

$C_{signal}O2(t)$ is the oxygen concentration corresponding to the uncorrected output signal of the oxygen analyzer 6 at time t;

$C_{measured}CO2(t)$ is the carbon dioxide concentration sensed at time t by the oxygen analyzer 6 after correction for span and offset; and $C_{signal}CO2(t)$ is the carbon dioxide concentration corresponding to the uncorrected output signal of the carbon dioxide analyzer 8 at time t.

Figure 6:
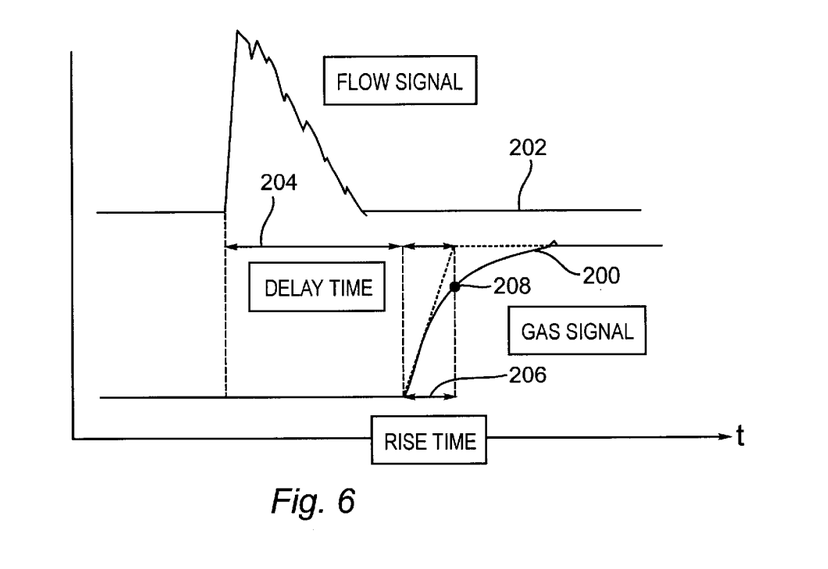
FIG. 6 is a graph showing the uncompensated output of a gas analyzer and the output of a flow sensor.

As taught by Noguchi et. al., "Breath-by-breath $\dot{V}CO_2$ and $\dot{V}O_2$ require compensation for transport delay and dynamic response," *J. Applied Physiology*, January 1982, p. 79–84, the output signal of a gas analyzer, such as the carbon dioxide analyzer 8 or the oxygen analyzer 6, closely follows first order kinetics in responding to a step change in gas concentration. FIG. 6 shows an uncompensated output signal 200 from a gas analyzer such as the carbon dioxide analyzer 8, and a flow signal 202 from a flow measuring device such as the pressure transducer 70. In order for a gas analyzer output signal to accurately reflect the original input signal—that is the actual gas concentration—the inverse Laplace transform must be applied to each output signal, as represented by the following equations:

$$C_{compensated}O2(t) = C_{measured}O2(t+D) + R*\left(\frac{dC}{dt}\right)_{(t+D)} \quad (7)$$

$$C_{compensated}CO2(t) = C_{measured}CO2(t+D) + R*\left(\frac{dC}{dt}\right)_{(t+D)}, \text{ where} \quad (8)$$

$C_{compensated}O2(t)$ is the oxygen concentration at time t after compensating for delay time and rise time;

$C_{measured}O2$ is as determined in equation (5) above;

$C_{compensated}CO2(t)$ is the carbon dioxide concentration at time t after compensating for delay time and rise time;

$C_{measured}CO2$ is as determined in equation (6) above;

t is the time of the measurement of the output signal from a gas analyzer;

D is the delay time 204; that is, the time it takes for the gas sample to travel from its sampled location to a gas analyzer;

R is the rise time 206, which is the time taken for the output signal from a gas analyzer to reach 67% of its full scale response; and $$\left(\frac{dC}{dt}\right)_{(t+D)}$$

is the derivative or instantaneous slope of the gas concentration output signal from a gas analyzer relative to time, at time (t+D).

Thus, it is necessary to determine D and R so that the inverse Laplace transform can be applied to breath by breath measurements from a patient to generate $C_{compensated}O2$ and $C_{compensated}CO2$ on a breath by breath basis.

As can be seen from FIG. 6, the delay time 204, or D, is the time that elapses between the time the gas to be measured begins to flow and the first detection of a change in gas concentration from baseline. D can be different for the oxygen analyzer 6 and the carbon dioxide analyzer 8. Preferably, the computer 18 calculates D for the carbon dioxide analyzer 8 by storing the time $t_1$ at which flow above baseline is detected by the flow sensor 56, then storing the time $t_2$ at which the first change in carbon dioxide concentration above baseline is detected by the carbon dioxide analyzer 8, and calculating the difference in those two stored times. The computer 18 calculates D for the oxygen analyzer 6 in the same way. To avoid determining incorrect values of $t_1$ and $t_2$ resulting from measurement noise, an arbitrary low threshold is set for the flow measurement and the gas concentration measurement. That is, $t_1$ is not measured until the flow reaches a threshold amount over baseline, and $t_2$ is not measured until gas concentration reaches a threshold amount over baseline. The values of $t_1$ and $t_2$ are then back-extrapolated using standard linear interpolation techniques after the slope of the signal has been determined as described above.

The rise time 206, or R, is determined by measuring the time elapsed from the beginning of the gas signal deviation from baseline (time $t_2$) until the time $t_3$ at which 67% of the full scale gas response has occurred. The 67% level of full concentration 208 is shown in FIG. 6, and is a predetermined constant. Preferably, the computer 18 calculates R for the carbon dioxide analyzer 8 by storing the time $t_2$ at which the first change in carbon dioxide concentration above baseline is detected by the carbon dioxide analyzer 8, then storing the time $t_3$ at which the gas signal 200 reaches the 67% level 208, and calculating the difference in these two stored times. The computer 18 calculates R for the oxygen analyzer 6 in the same way.

Measurement of the rise time R and the delay time D is necessary in order to compensate for the measurement error inherent in current gas analyzers exhibiting first-order kinetics. Additionally, calibration factors must be calculated for each gas analyzer in order to accurately convert its output signals to gas concentrations.

The result of calibration is a set of calibration factors stored in the computer 18: R, D, SlopeO2, OffsetO2, SlopeCO2, and OffsetCO2.

After calibration is complete, the computer 9 preferably generates a graph or a tabular chart, or both, on the display 20, allowing the operator to visually check that calibration was successful. If a graph is shown on the display 20, it preferably applies the calibration factors and the inverse Laplace transform disclosed above to the gas analyzer output signals measured during calibration, in a manner that will be disclosed in greater detail below with regard to the patient exercise test. Proper operation is indicated if the leading edges of the $O_2$ concentration and $CO_2$ concentration are lined up with the flow rate signal, and if the leading edges of the O2 concentration and CO2 concentration signals are nearly vertical and free from overshoot.

Preferably, calibration is performed once at the beginning of each testing day. Daily calibration is preferred because it balances the need for accurate testing with the time required for calibration. However, if desired, calibration may be performed more frequently. In addition, calibration may be performed less frequently if gas sensors and analyzers are used which do not drift substantially with time. In that case, the operator may choose to perform a verification step instead of calibration.

Verification

Verification is a process by which the operator of the test station 2 can verify that the rise time R and the delay time D measured during calibration, and the slope and offset calculated during calibration, are correct. Typically, calibration is performed when the test station 2 is first activated on a day in which testing is to be conducted, and verification is periodically performed afterward to ensure that the calibration factors are correct and no drift has occurred. Of course, either calibration or verification can be performed at any time to ensure that the calibration factors are accurate.

Verification proceeds identically to calibration, with the exception that delay time and rise time are not measured, and slope and offset are not calculated. Instead, the delay time and rise time previously measured during calibration and stored in the computer 18, and the slope and offset previously calculated during calibration and stored in the computer 18, are applied to the calibration gas measured during the simulated breath. The operator can then inspect the results on the display 20 to ensure that the integrated function of the exercise test apparatus 4 is operating properly. Proper operation is indicated if the leading edges of the $O_2$ concentration, $CO_2$ concentration, and flow rate signals are lined up, and if the rise times are free from overshoot. If the operator is not satisfied with the results of verification, calibration should be initiated or repeated.

Patient Date Entry

A set of patient data items is entered into the computer 18, which preferably stores them. This patient data set preferably includes the patient's name, date of birth, height, weight, gender and medication usage, as well as the type of work device used or to be used. This data is used to calculate normal reference values including but not limited to maximum heart rate, Peak $\dot{V}O_2$, anaerobic threshold, and maximum breathing capacity. Calculation of these values from the patient data set entered in this step is well known in the medical literature. Preferably, the patient data set is stored with the computer 18 and may be used for future tests, eliminating the need to reenter the patient data set for a given patient if that patient is retested in the future. The patient data set preferably may be retroactively edited for any individual test.

Patient Testing

The operator may choose to perform exercise testing alone, or in combination with pre-exercise or post-exercise spirometry testing. Spirometry may also be performed alone if desired. The results of exercise testing, and of pre-exercise and post-exercise spirometry, are preferably stored in the computer 18. Spirometry alone may be performed with a given patient if an exercise test was previously done for that patient without spirometry. The spirometry results are preferably stored in the computer 18 in association with the exercise test results for each tested patient. Spirometry and exercise testing will now be described in detail.

Spirometry

Spirometry data is used to calculate the patient's maximum breathing capacity (MBC) and is an excellent screening test for many pulmonary disorders. By integrating the ability to first make these resting measurements prior to performing an exercise test, then using this data to predict the patient's MBC, then assessing the ventilatory and gas exchange responses of a patient during exercise and comparing those responses to the patient's MBC, CPX is better able to distinguish pulmonary from cardiac causes of exercise limitation as well as make a more comprehensive evaluation of the respiratory system.

Figure 2:
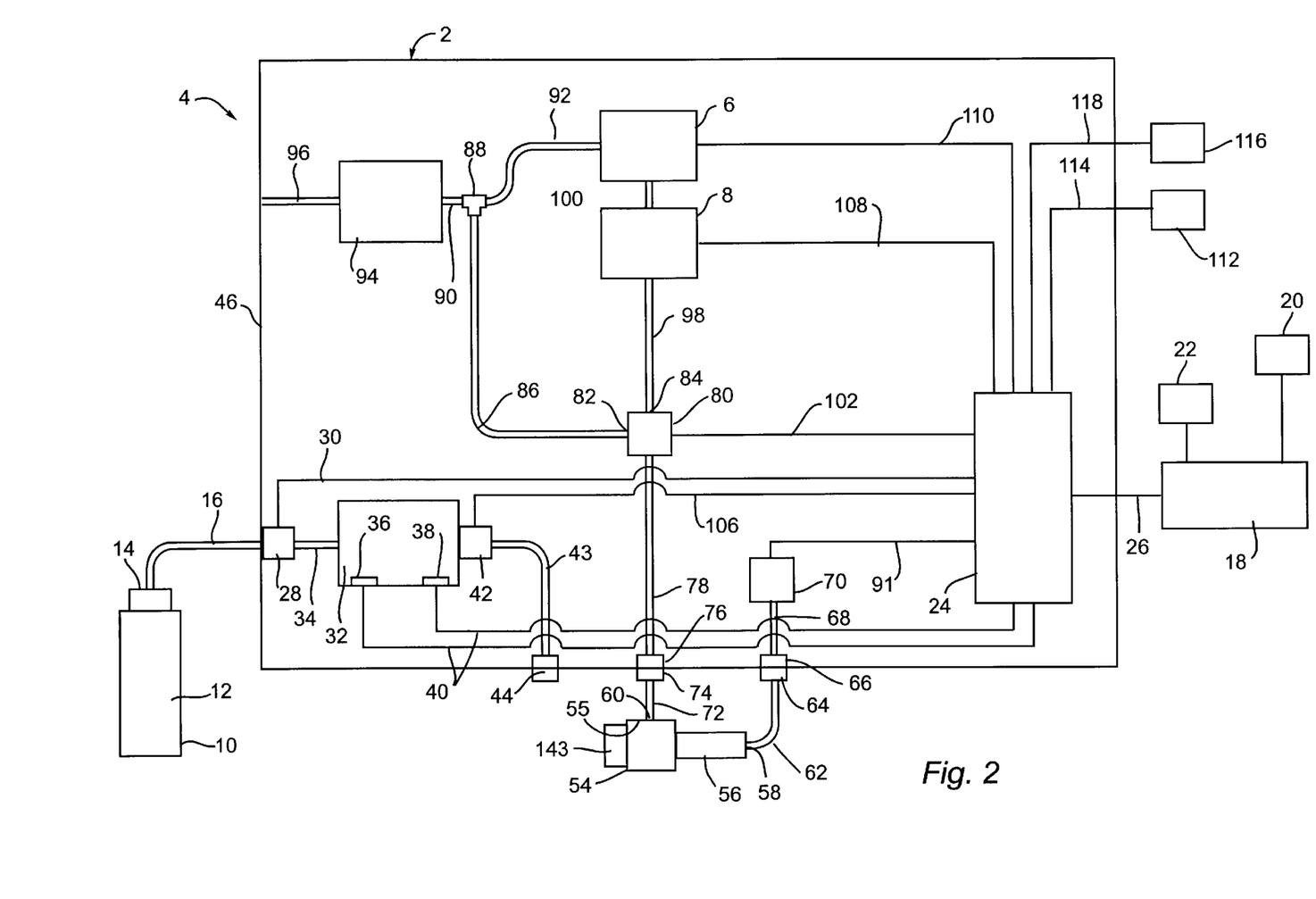
FIG. 2 is a schematic view of an exercise test apparatus, configured with a mouthpiece for spirometry.

During spirometry, the flow sensor 56 need not be attached to the adapter 54. However, as in calibration, the flow sensor outlet hose 62 is attached at one end to the flow sensor outlet port 58 on the flow sensor 56, and at the other end to the first flow sensor outlet hose connector 64. The first flow sensor outlet hose connector 64 is attached to the shell 46 of the test station 2. A pressure transducer hose 68 is located within the test station 2, and is connected at one end to the first flow sensor outlet hose connector 64 and at the other end to a pressure transducer 70.

Initially, the operator zeroes the pressure transducer 70 by keeping the flow sensor 56 still, for example, by placing the flow sensor 56 on the calibration port 44 or on a surface in a location where the air is still. The flow through the flow sensor 56 while it is at rest is effectively zero. The operator enters a command for zeroing into the computer 18. Analog output from the pressure transducer 70 is transmitted over the pressure transducer signal wire 91 to the A/D converter 24, where it is converted to digital form and transmitted to the computer 18 via the external communications cable 26. The output signal from the pressure transducer 70 during zeroing corresponds to a flow rate of zero. The computer averages that output signal over a short period of time, and the computer 18 then equates the averaged output signal from the pressure transducer 70 with zero flow. The value of that averaged output signal is stored in the computer 18.

The spirometry test then begins. Referring to FIG. 2, the patient preferably places the flow sensor 56 into his or her mouth, with or without a mouthpiece 143. If the mouthpiece 143 is used, it is attached to the adapter 54, preferably by a pressure fit against an inner surface 57 of the adapter 54. It should be noted that the adapter 54 preferably accommodates a pressure-fit attachment to the calibration port 44 or the mouthpiece 143.

The patient then makes a maximum expiratory effort into the adapter 54. That is, the patient, exhales as forcefully as possible for as long as possible into the adapter 54. The two most important variables measured during spirometry are Forced Expiratory Volume in 1 Second (FEV1) and Forced Vital Capacity (FVC), which is the total exhaled breath volume during a maximum expiratory effort. The FEV1 and FVC measurements are well known in the medical literature. As stated above, the computer 18 determines the volume of the flow through the flow sensor 56 by integrating the measured flow rate with respect to time. The patient's maximum breathing capacity (MBC) is then calculated from the FEV1 measurement, based on published equations. Karlman Wasserman et. al., *Principles of Exercise Testing and Interpretation* at 79 (1984). The FEV1, FVC and MBC for that maximum expiratory effort are then displayed on the display 20.

Preferably, the patient then repeats a maximum expiratory effort until two consistent results are recorded. The display 20 preferably includes an incentive bar or other graphic which demarcates the patient's previous best effort, to encourage the patient to perform maximum expiratory efforts. The computer 18 compares the spirometry results between each trial to ensure that they are within the standards of the American Thoracic Society. American Thoracic Society Board of Directors, Robert O. Crapo et. al., "Standardization of Spirometry: 1994 Update," *Am. J. Respiratory and Critical Care Medicine* 152:1107–1136 (1995). Consistent results between trials indicate that the patient has in fact exerted a maximum expiratory effort in each trial. After three or more trials and two consistent results within the standards of the American Thoracic Society, there is no need for the patient to repeat a maximum expiratory effort.

The data for the best trial are preferably displayed on the display 20 as a flow vs. volume curve, and the numerical values for FEV1 and FVC are shown on the graph as well as in tabular form with reference values and predicted values. The values of FEV1, FVC, and MBC are stored in the computer 18.

Spirometry may optionally be omitted if the patient has previously been tested and the patient's previous spirometry data has been retained on the computer 18. Otherwise, omission of spirometry, while allowable within the scope of the present invention, results in the loss of diagnostic information.

Patient Exercise Test

Figure 3:
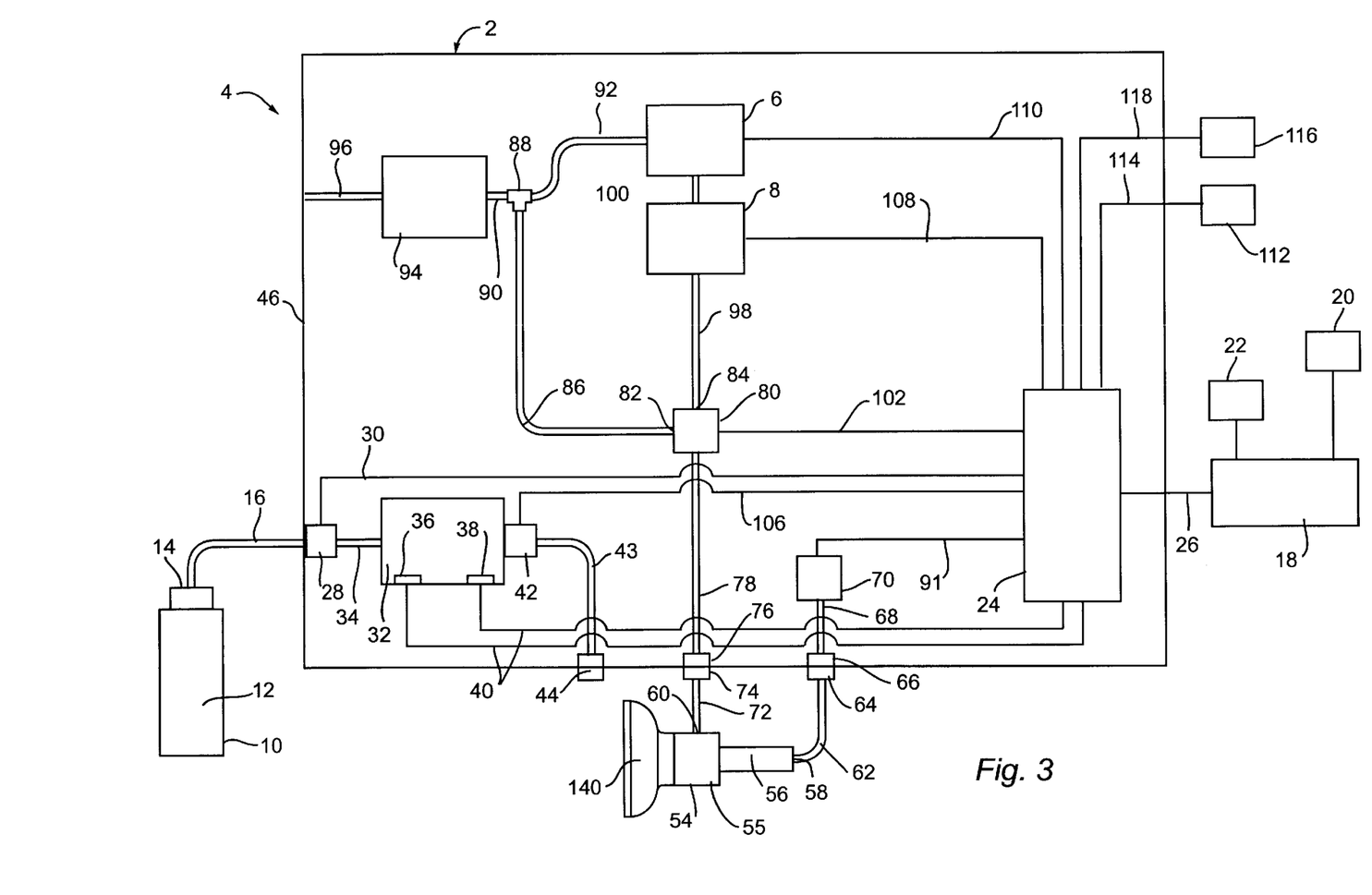
FIG. 3 is a schematic view of an exercise test apparatus, configured with a face mask for spirometry and exercise testing.
Figure 4:
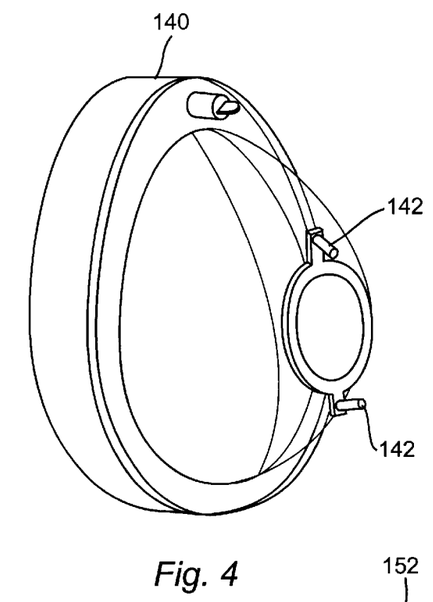
FIG. 4 is a perspective view of a face mask for use with a patient.

Referring to FIG. 3, to begin the patient exercise test, a face mask 140 is preferably placed over the patient's mouth and nose. Optionally, the mouthpiece 143 and noseclips (not shown) may be used. The size of the face mask 140 should be selected by the operator to be appropriate for the patient to allow a tight gas seal around the patient's mouth and nose. The face mask 140 preferably includes two headstrap pins 142. The headstrap pins 142 preferably extend from an outer surface 141 of the face mask 140 in a direction substantially away from the patient. While two headstrap pins 142 are preferred, a plurality of headstrap pins may be included on the face mask 140 if desired.

Figure 5:
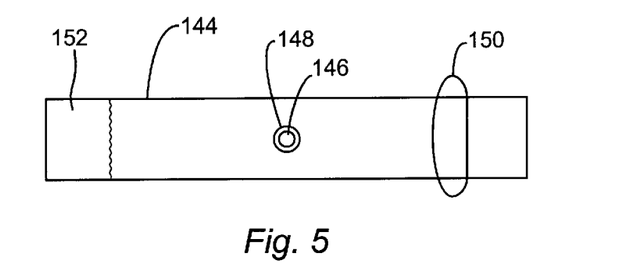
FIG. 5 is a top view of a headstrap for securing the face mask to a patient.

Referring to FIG. 5, in a preferred embodiment, one or more headstraps 144 are used to secure the face mask 140 to a patient. Each headstrap 144 preferably defines a hole 146, which is preferably surrounded by a grommet 148 that may be constructed of metal, plastic, or other durable material. The headstrap or headstraps 144 are preferably composed of elasticized material at least partly covered with quick-release attachment means, such as VELCRO® material. A loop 150 is attached at or near one end of the headstrap 144. The other end of the headstrap 144 possesses an attachment region 152 also having quick-release attachment means, such as VELCRO® material.

To secure the face mask 140 to a patient, the face mask 140 is placed over the patient's mouth and nose. The headstrap 144 is then placed such that one of the headstrap pins 142 goes through the hole 146. Optionally, the face mask 140 and headstrap 144 can be designed to interconnect via a plurality of headstrap pins 142 and holes 146. Each end of the headstrap is then brought to the rear of the patient's head. The end of the headstrap 144 possessing the attachment region 152 is pulled through the loop 150 until a snug but comfortable fit is achieved against the patient's head. The end of the headstrap 144 possessing the attachment region 152 is then folded over to come into contact with the headstrap 144, thereby becoming attached to it via the quick-release attachment means associated with the attachment region 152 and the headstrap 144. Thus, the headstrap 144 can be adjusted and secured in a single step. Another advantage of the headstrap 144 is that it can be quickly and easily removed by a patient or the operator simply by lifting the headstrap 144 over the corresponding headstrap pin 142, because the headstrap 144 is held onto the headstrap pin 144 solely due to the tension in the headstrap 144.

Preferably, one headstrap 144 is positioned around the patient's head over the ears and another headstrap 144 is positioned around the patient's head under the ears, providing for a secure fit and minimizing fit difficulties arising from varying head sizes and shapes, and from head or facial hair.

Referring to FIG. 3, the face mask 140 is connected to the end of the adapter 54, preferably by a pressure fit. The adapter 54 is connected to the test station 2 via the sampling hose 72, and the flow sensor 56 is connected to the test station 2 via the flow sensor outlet hose 62, in the same manner as during calibration. As can be seen by a comparison of FIG. 1 and FIG. 3, the configuration of the exercise test apparatus 4 during calibration simulates the configuration of the exercise test apparatus 4 during patient testing, without any change in pneumatic circuitry which could affect the delay and rise times.

An oximeter 112 is preferably non-invasively attached to the patient, and measures blood oxygen saturation. The non-invasive oximeter 112 is known in the art, and may be readily obtained in the market. The oximeter 112 is connected to an oximeter wire 114, through which the oximeter 112 transmits data to the A/D converter 24. The analog blood oxygen saturation data is then converted to digital form and transmitted through the external communications cable 26 to the computer 18. Oxygen saturation is the percent of hemoglobin loaded with oxygen. The actual amount of $O_2$ carried by a volume of blood (that is, $O_2$ content) is dependent on both oxygen saturation and hemoglobin concentration. Low oxygen saturation ($SaO_2$) reflects poor lung function and will contribute to poor exercise capacity.

Preferably, the oximeter 112 is also capable of measuring the pulse of the patient, and transmits pulse data to the A/D converter 24 for transmission to the computer 18 in the same manner as the oximeter data. However, a heart rate monitor 116, such as an electrocardiograph (EKG) or telemetry-type pulse detector may be optionally connected to the test station 2 for more precise measurement of the patient's heart rate. If the heart rate monitor 116 is used, it is connected to the A/D converter 24 via a heart rate monitor wire 118. The analog signals from the heart rate monitor 116 are then converted to digital form and transmitted through the external communications cable 26 to the computer 18. If the analog heart rate monitor 116 outputs waveforms rather than heart rate, the computer 18 converts this information into heart rate by measuring the interval between successive beats.

The operator then begins the exercise test via the computer 18. The computer 18 issues a command to the purge valve 80 to close the purge outlet 82 and open the gas analysis outlet 84. This command is transmitted through the external communications cable 26 to the A/D converter 24, which translates the command into analog form and sends a signal through the purge valve command wire 102 to the purge valve 80. If the purge outlet 82 is already closed and the gas analysis outlet 84 is already open, this condition is maintained. The pump 94 is already on, as described earlier.

After the operator initiates the test, the computer 18 begins collecting data on a breath-by-breath basis from the pressure transducer 70, the carbon dioxide analyzer 8, the oxygen analyzer 6, and the oximeter 112, as well as from the heart rate monitor 116 if used. Preferably, a resting, baseline period of observation is recorded at the beginning of the test.

The patient then begins exercise on an exercise machine (not shown), preferably a treadmill or stationary bicycle. However, other exercises or exercise machines may be used so long as they allow the patient to work continuously at incremental work loads. Optionally, the computer 18 is electronically connected to such an exercise machine, allowing the computer 18 to control its speed and/or monitor the patient's work level.

The patient's exhaled breath passes from the patient's nose and/or mouth through the face mask 140 into the adapter 54. A portion of the patient's breath thus entering the adapter 54 is drawn off from the adapter 54 through the gas analysis outlet port 60, due to the suction of the pump 94 which is in flow communication with the gas analysis outlet port 60. That portion of the patient's exhaled breath thus travels through the sampling hose 72, the first gas analysis outlet hose connector 74, the internal gas transfer hose 78, the purge valve 80, and the gas analysis inlet hose 98 to the carbon dioxide analyzer 8. The carbon dioxide analyzer 8 measures the amount of $CO_2$ in the patient's exhaled breath, and transmits that analog measurement to the A/D converter 24 through the carbon dioxide analyzer wire 108. The A/D converter 24 converts that analog signal to a digital signal and transmits it to the computer 18 via the external communications cable 26.

The patient's breath then flows from the carbon dioxide analyzer 8 to the oxygen analyzer 6 via the analyzer connector hose 100. Preferably, the carbon dioxide analyzer 8 and the oxygen analyzer 6 are arranged in series in that order, but they may be arranged in the opposite order or in parallel if desired, at the penalty of more-complex plumbing within the test station 2. The oxygen analyzer 6 measures the amount of $O_2$ in the patient's exhaled breath, and transmits that analog measurement to the A/D converter 24 through an oxygen analyzer wire 110. The A/D converter 24 converts that analog signal to a digital signal and transmits it to the computer 18 via the external communications cable 26.

The patient's exhaled breath is then drawn from the oxygen analyzer 6 through the gas analyzer outlet hose 92, the T-connector 88, and the pump inlet hose 90 into the pump 94, where it is then expelled from the test station 2 through the pump outlet hose 96.

The flow sensor 56 attached to the adapter 54 is in flow communication with the pressure transducer 70 via the flow sensor outlet port 58, the flow sensor outlet hose 62 and the pressure transducer hose 68. Measurements from the pressure transducer 70 are transmitted to the A/D converter 24 through the pressure transducer signal wire 91. The A/D converter 24 converts that analog signal to a digital signal and transmits it to the computer 18 via the external communications cable 26. The computer 18 then converts the pressure measurement into a flow measurement as described above. Thus, the flow rate and overall volume exhaled during each breath are determined.

While the patient exercises, the oximeter 112 measures the patient's blood oxygen saturation level. The oximeter 112 generates an analog electrical signal corresponding to the measured blood oxygen saturation level, which travels along the pulse oximeter wire 114 to the A/D converter 24.

If the oximeter 112 is used to measure the patient's heart rate as well, it also generates an analog electrical signal based on the patient's heart rate, which travels along the oximeter wire 114 to the A/D converter 24. The A/D converter 24 converts that analog signal to a digital signal and transmits it to the computer 18 via the external communications cable 26.

If the patient's pulse rate is measured by a heart rate monitor 116, an analog electrical signal travels through the heart rate monitor wire 118 to the A/D converter 24. The A/D converter 24 converts that analog signal to a digital signal and transmits it to the computer 18 via the external communications cable 26. If the analog heart rate monitor 116 outputs waveforms rather than heart rate, the computer 18 converts this information into heart rate by measuring the interval between successive beats.

The patient's respiratory rate and tidal volume (the volume of each individual breath) are calculated by the computer 18 based on the output signals of the pressure transducer 70. One breath is preferably defined as the interval between two successive inspiratory efforts. The pressure transducer 70 detects an inspiratory effort by noting the time when the gas pressure it measures reverses direction. Preferably, the computer 18 then calculates the time difference between each inspiratory effort and the succeeding one, and converts that time into terms of breaths per minute. Tidal volume is also calculated from the signal output of the pressure transducer 70. As described above, the pressure transducer 70 measures flow based on the pressure difference between ambient air and the pressure experienced by the flow sensor 56. The computer 18 determines the flow for a single breath by converting output from the pressure transducer 70 to flow rate over the time between the two successive inspiratory efforts that define that breath, then integrating that flow rate with respect to time to determine tidal volume.

In a preferred embodiment, during the exercise test, the computer 18 applies the stored calibration factors to the output signals on a breath-by-breath basis from the oxygen analyzer 6 and the carbon dioxide analyzer 8. As described above, Equation (7) is used to determine the concentration of oxygen sensed by the oxygen analyzer 6 and Equation (8) is used to determine the concentration of carbon dioxide sensed by the carbon dioxide analyzer 8. However, the computer 18 can also store the raw breath-by-breath output signals from the oxygen analyzer 6 and the carbon dioxide analyzer 8, and apply the calibration factors to that data after the exercise test has been completed. The computer 18 synchronizes the exhaled air flow signal (computed from the output signals from the pressure transducer 70) with the corresponding instantaneous compensated gas concentrations for O2 and CO2. The computer 18 then multiples the instantaneous compensated oxygen concentration at time t by the instantaneous flow rate at time t, resulting in a product O2Flow. Similarly, the computer 18 multiples the instantaneous compensated carbon dioxide concentration at time t by the instantaneous flow rate at time t, resulting in a product CO2Flow. By integrating O2Flow and CO2Flow with respect to time over the duration of the exhaled breath, the computer 18 determines the volume of oxygen consumed and carbon dioxide produced over that breath. By then dividing those volumes by the measured duration of the entire breath cycle, the computer 18 calculates the rate of oxygen consumption and of carbon dioxide production. Appropriate correction factors for temperature and water vapor content are applied, as are known in the literature.

During the test, the computer 18 preferably displays on the display 20 the breath-by-breath measurements and calculations of $\dot{V}E$, $\dot{V}O_2$, $\dot{V}CO_2$, respiratory rate, heart rate, respiratory exchange ratio (the ratio of $\dot{V}CO_2$ to $\dot{V}O_2$, also referred to as RER) and $SaO_2$, in tabular form. Further, the computer 18 preferably graphs on the display 20 heart rate relative to $\dot{V}O_2$, with the expected maximmum $\dot{V}O_2$ and heart rate displayed for reference. Other relationships may be graphed during the course of the test, if desired.

The operator terminates the test when the patient has worked to a predetermined heart rate (such as a percentage of the maximum predicted heart rate), the patient exhibits a potentially dangerous change in heart rate, O2 saturation, or other monitored or measured parameters, or the patient stops exercising due to symptoms such as exhaustion, breathlessness, distress, or other reasons. Data recording continues until the operator inputs a prompt to the computer 18 indicating that the test is over. The operator then inputs into the computer 18 the reason for test. termination, which is stored in the computer 18. This input is preferably made by selecting from a predetermined list of options provided by the computer 18. This information is preferably included in the analysis of the patient's test results.

Analyzing and Displaying Test Results

In a preferred embodiment, the computer 18 displays selected test data in real time on the display 20. At the completion of the test, the computer 18 displays complete test results on the display 20 and prints them on the printer 22.

With respect to the data gathered on a breath-by-breath basis, the computer 18 preferably utilizes a three-breath rolling average to reduce measurement noise. That is, data taken during each breath is averaged with data from the two preceding breaths in calculating variables based on that data. However, more than three breaths may be averaged, or other methods of noise reduction may be used to reduce measurement noise if desired.

The computer 18 first uses the height, weight, age and gender information input during the earlier process of patient data entry to calculate predicted values for FEV1, FVC, ideal body weight, peak $\dot{V}O_2$, anaerobic threshold and maximum heart rate, using well-known published regression equations. The computer 18 then adjusts the predicted peak $\dot{V}O_2$ and anaerobic threshold, depending on the type of exercise performed, based on published data. The computer 18 may optionally adjust the predicted peak $\dot{V}O_2$ and anaerobic threshold based on the type of exercise machine used, such as a stationary bicycle or a treadmill.

The computer 18 compares the full range of recorded values of $\dot{V}O_2$ over the entire exercise test to determine the maximum value of $\dot{V}O_2$, referred to as peak $\dot{V}O_2$, and stores peak $\dot{V}O_2$, as well as the time that peak $\dot{V}O_2$ was achieved. The computer 18 then locates the values of $\dot{V}CO_2$, heart rate, $SaO_2$, $\dot{V}E$, and tidal volume (the volume of a single breath) measured at the time that peak $\dot{V}O_2$ occurred, and stores them. Optionally, work rate at peak $\dot{V}O_2$ is stored as well.

After the exercise test, the computer 18 preferably produces a series of four graphs on the display 20. Each graph preferably plots individual data points, one per breath, preferably averaged over a three-breath rolling average as described previously. All of these four graphs may be printed together on one sheet of paper for convenience of use and interpretation.

1. Heart rate v. $\dot{V}O_2$ and Stroke Volume vs. $\dot{V}O_2$

Figure 7:
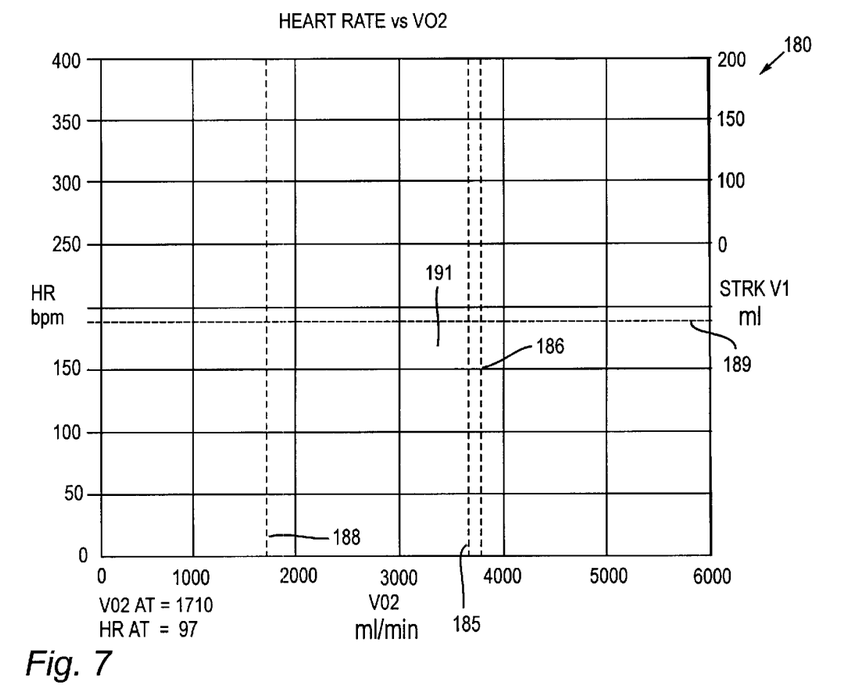
FIG. 7 is a composite graph of heart rate vs. $\dot{V}O_2$ and stroke volume vs. $\dot{V}O_2$.

Referring to FIG. 7, the first graph 180 plots measured heart rate and calculated stroke volume on the Y axis. Stroke volume is calculated by estimating cardiac output in liters/ min from $\dot{V}O_2$ based on standard published equations, then dividing the cardiac output by the patient's heart rate. The X axis plots $\dot{V}O_2$. Additionally, the first graph 180 preferably identifies observed peak $\dot{V}O_2$ 185, predicted peak $\dot{V}O_2$ 186, measured anaerobic threshold 188, predicted maximum heart rate 189, and observed maximum heart rate 191. The rate at which heart rate increases relative to $\dot{V}O_2$ is the chronotropic response, which is not readily appreciated when using testing techniques which do not directly measure $\dot{V}O_2$. An abnormal relationship between heart rate and $\dot{V}O_2$ (e.g., too slow, too fast or nonlinear) is an independent risk factor for poor outcome in cardiomyopathy and coronary artery disease. This relationship does not hold if the patient is taking beta blockers or other drugs that slow the heart rate increase relative to $\dot{V}O_2$ A high chronotropic response indicates deconditioning if peak $\dot{V}O_2$ is normal, and cardiac disease if peak $\dot{V}O_2$ is impaired. A low chronotropic response can indicated fitness if peak $\dot{V}O_2$ is greater than the predicted value, or disease, if peak $\dot{V}O_2$ is impaired. The graph also indicates the $\dot{V}O_2$ level and the corresponding heart rate at which the anaerobic threshold occurs. This heart rate may be used for guiding aerobic training regimens or programs. The difference between the measured peak $\dot{V}O_2$ 185 and the predicted peak $\dot{V}O_2$ 186 can also be easily seen. The first graph 180 summarizes for the clinician at a glance a great deal of important information regarding the metabolic and cardiovascular function of a patient.

2. $\dot{V}E$ v. $\dot{V}CO_2$ and $SaO_2$ vs. $\dot{V}CO_2$

Figure 8:
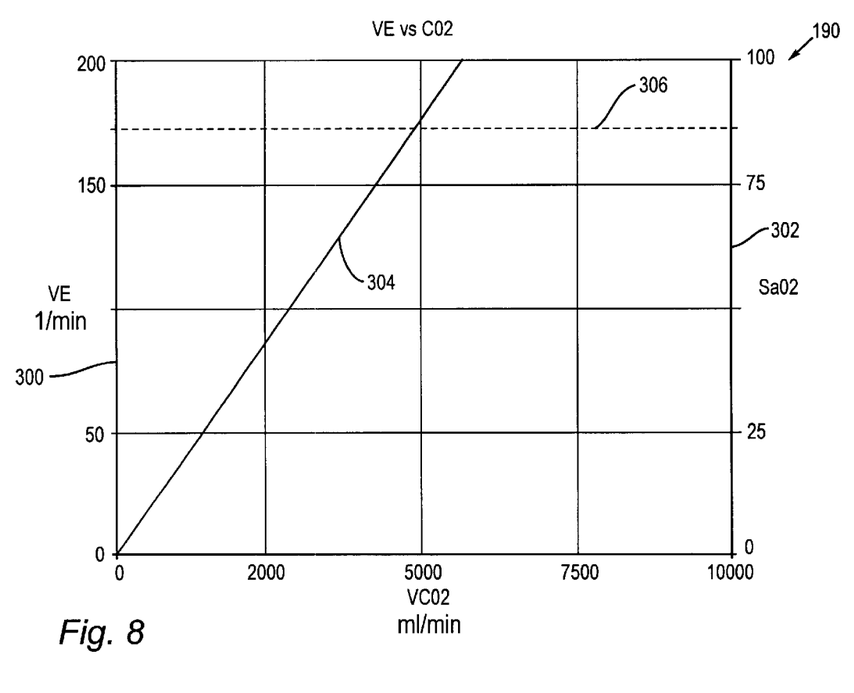
FIG. 8 is a composite graph of $\dot{V}E$ vs. $\dot{V}CO_2$ and $SaO_2$ vs. $\dot{V}CO_2$.

Referring to FIG. 8, the second graph 190 plots $\dot{V}E$ on a first Y axis 300 and $SaO_2$ on a second Y axis 302. The X axis plots $\dot{V}CO_2$. Preferably, a reference line 304 representing a $\dot{V}E/\dot{V}CO_2$ ratio of 34.0is plotted because any ventilation above this slope indicates heart or lung disease, since both result in wasted ventilation due to relatively poor blood flow serving a region of relatively well-aerated lung. Wasted ventilation occurs when the patient has to breathe excessively in order to clear carbon dioxide from the lung, due to low blood flow in the lung. Heart disease may be distinguished from lung disease if an abnormally high $\dot{V}E/\dot{V}CO_2$ relationship is not accompanied by $O_2$ desaturation. Lung disease almost invariably will be manifested by both $O_2$ desaturation and/or high ventilation. Although other diseases or conditions, such as hyperventilation, anemia, or metabolic acidosis, may cause high ventilation relative to $\dot{V}CO_2$ without desaturation, other information helps make the distinction. Any drop in $O_2$ saturation greater than 3–4% over the course of progressive exercise is abnormal, providing that the test station 2 is operating properly. The limit of breathing capacity, MBC, is estimated from the resting FEV1 measured during spirometry, and this limit is represented as an MBC line 306 parallel to the X-axis. The difference between the MBC line 306 and the maximum $\dot{V}E$ achieved, which is clearly visible at a glance on the second graph 190 at the maximum $\dot{V}E$ point 308, represents the "breathing reserve" and further helps delineate whether limited breathing capacity is the cause of the exercise limitation. If the breathing reserve is exhausted during the test, lung disease may be inferred. For this reason, spirometry is beneficial and is advantageously performed before cardiopulmonary exercise testing.

3. $\dot{V}CO_2$ v. $\dot{V}O_2$, $\dot{V}E/\dot{V}CO_2$ v. $\dot{V}O_2$, and $\dot{V}E/\dot{V}O_2$ vs. $\dot{V}O_2$ Referring to FIG. 9, the third graph 200 plots $\dot{V}O_2$ on the X axis and $\dot{V}CO_2$ on the first Y axis 310. The ratios of $\dot{V}E/\dot{V}CO_2$ and $\dot{V}E/\dot{V}O_2$, which are referred to as ventilatory equivalents for $CO_2$ and $O_2$, are plotted on the second Y axis 312. The third graph 200 shows the data with which the ventilatory anaerobic threshold is determined and allows the operator to see graphically the quality of the data upon which the calculations are based.

Figure 9:
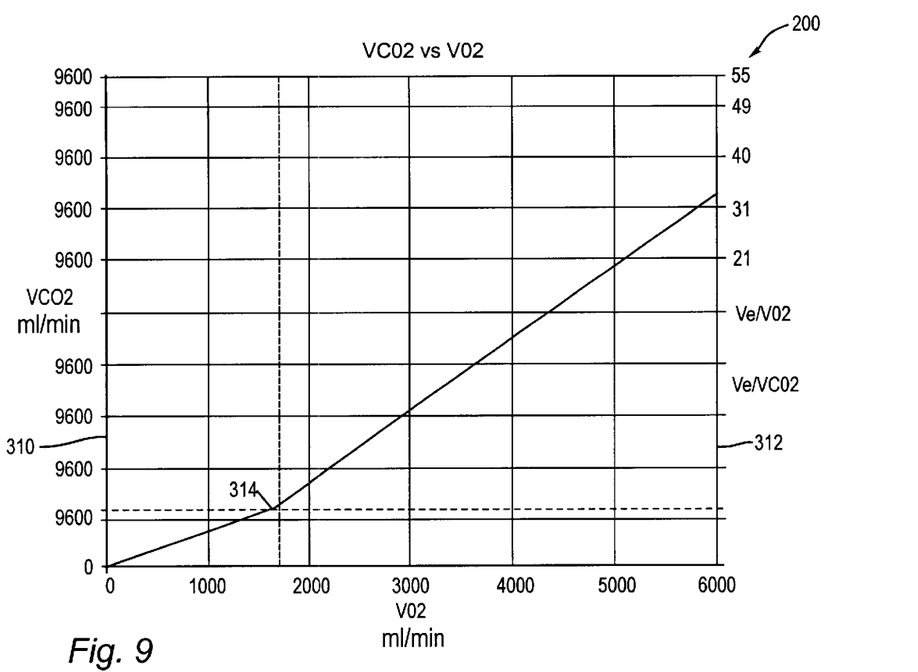
FIG. 9 is a composite graph of $\dot{V}CO_2$ vs. $\dot{V}O_2$, $\dot{V}E/\dot{V}CO_2$ v. $\dot{V}O_2$, and $\dot{V}E/\dot{V}O_2$ vs. $\dot{V}O_2$.

Anaerobic threshold (AT) is a submaximal indication of cardiovascular fitness that correlates with peak $\dot{V}O_2$. It provides complementary diagnostic and prognostic information, and predicts performance in endurance athletes. AT is also an effort-independent parameter. The computer 18 preferably calculates AT with the V-slope algorithm described in William L. Beaver et al., "A new method for detecting anaerobic threshold by gas exchange," *J. Applied Physiology* 60:2020–2027 (1986). The point of greatest inflection in the curve is determined; this inflection point 314 corresponds with the work level ($\dot{V}O_2$) at which excess $CO_2$ is produced due to the buffering of lactic acid, which is produced in increased quantities as exercise continues. That point of greatest inflection corresponds to the patient's anaerobic threshold. On the ventilatory equivalent graphs, at the anaerobic threshold, the ratio of $\dot{V}E/\dot{V}O_2$ will start to increase while the $\dot{V}E/\dot{V}CO_2$ line remains stable or begins to decrease. This transition point should correspond to the V-slope inflection point. The operator may visually determine if both points on this graph are aligned; alignment means there is more confidence in the AT data.

AT is an indicator of the patient's level of physical conditioning. A normal, healthy patient has a ratio of the $\dot{V}O_2$ associated with AT the peak $\dot{V}O_2$ (the "AT ratio") of 40–60%. The AT ratio may rise to 70–80% for well-conditioned endurance athletes. A patient with a normal AT ratio, but a low peak $\dot{V}O_2$ and a low AT compared to his or her predicted AT, has a cardiovascular or metabolic problem. In contrast, a patient exhibiting low peak $\dot{V}O_2$ with a normal AT and a high AT ratio may have a pulmonary problem, pain, or other limiting factors, but likely not left ventricular dysfunction.

4. Heart rate & $\dot{V}O_2$ v. time

Figure 10:
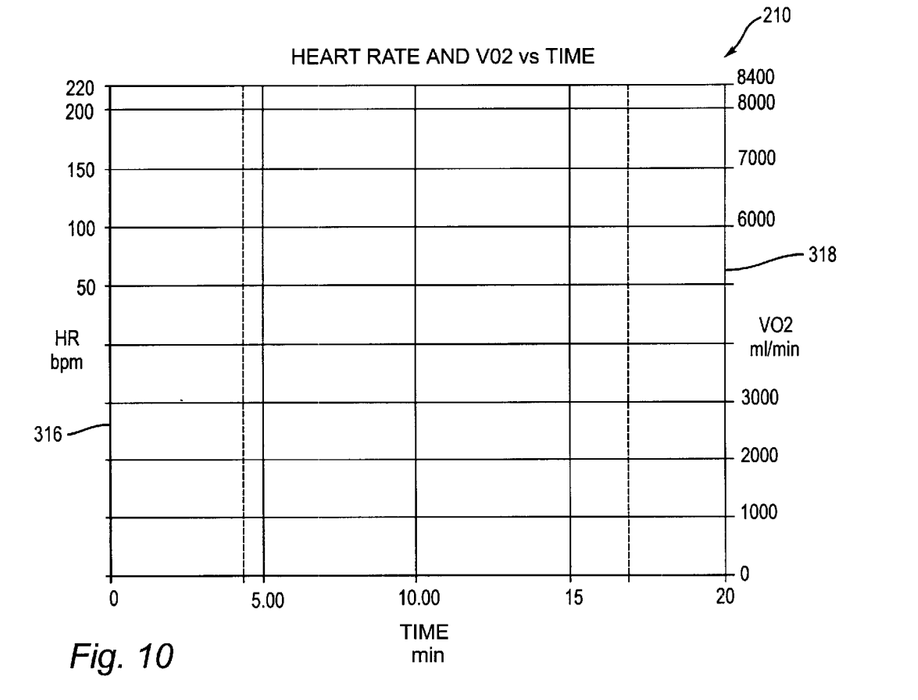
FIG. 10 is a graph of heart rate and $\dot{V}O_2$ vs. time.

Referring to FIG. 10, the fourth graph 210 plots heart rate on the first Y axis 316 and $\dot{V}O_2$ on the second Y axis 318, against time on the X axis. The graph also shows the peak $\dot{V}O_2$ determined by the computer 18. The graph also depicts the time at which the AT occurred, and shows whether the patient's changes in work intensity are gradual or abrupt, or whether the patient's aerobic capacity plateaus at a certain level.

The selection of data and the grouping of relationships between parameters are intimately linked to the logic of the analysis algorithms. Aerobic exercise capacity is objectively measured by $\dot{V}O_2$, which is more accurate than estimating it from work duration or intensity. Measuring the anaerobic threshold and relating it to peak $\dot{V}O_2$ helps distinguish metabolic and cardiovascular disorders from other factors such as poor motivation, musculoskeletal pain, or lung disease. Lung disease can be distinguished from heart disease by the presence of $O_2$ desaturation with excessive ventilation. Pulmonary disease is indicated by abnormal resting spirometry measurements, abnormal ventilatory and $O_2$ saturation responses during exercise, and limitation of breathing reserve at the end of exercise. Breathing reserve is generally not exhausted in normal individuals or cardiac-limited subjects. All of these relationships are evident on the first graph 180, the second graph 190, the third graph 200, and the fourth graph 210. The detailed numerical data is also available, so that skilled practitioners can draw their own conclusions.

5. Other analysis

The computer 18 records the $SaO_2$ levels monitored during the exercise test by the oximeter 112. The $SaO_2$ measured during the exercise test should not decrease by more than 4% during the exercise test; it if does, lung disease or pulmonary vascular disease may be irresponsible. The computer 18 calculates the percentage increase or decrease in $SaO_2$ measured during the exercise test by comparing the $SaO_2$ measurements during the baseline period of the test with the $SaO_2$ measurements at peak $\dot{V}O_2$. If $SaO_2$ decreases by more than 4% during the exercise test, the computer 18 indicates this on the display 20 and/or in a report printed on the printer 22 after the test. The $SaO_2$ levels measured during the test are also displayed on the second graph 190, as described above. The operator can visually inspect the second graph 190 to determine if any unusual variations in $SaO_2$ occurred during the test.

The computer 18 also compares the predicted maximum heart rate with the measured maximum heart rate. The difference between them is called the heart rate reserve, which may indicate relative cardiovascular stress.

Preferably, the computer 18 generates a narrative report and optionally prints it on the printer 22, identifying the key variables discussed above and their deviations, if any, from normal, and indicates the implications of these abnormalities.

While the word "patient" has been used in this application, this does not limit the scope of the present invention to a medical setting. The present invention may also be used in health clubs, athletic training programs, military or police screening and training, disability evaluation and other settings where it is desirable to measure or improve physical condition and endurance.

Reference to the A/D converter 24 does not prohibit the use of digital sensors, digital command apparatus, or a set of individual A/D converters instead of or in addition to the single A/D converter. The single A/D converter 24 working with analog sensors and actuators is preferred due to the cost savings and simplicity of using merely one, rather than a plurality.

Reference to electronic wiring in the present invention is made for clarity of description, and does not prohibit wireless connections between the electronic parts disclosed herein. Wires are preferred due to their cost savings and simplicity at the present time.

A preferred method for measuring and analyzing exhaled breath for diagnosis of cardiopulmonary disease, and many of its attendant advantages, has thus been disclosed. It will be apparent, however, that various changes may be made in the steps of this method and their arrangement without departing from the spirit and scope of the invention, the steps hereinbefore described being merely a preferred or exemplary embodiment thereof. Therefore, the invention is not to be restricted or limited except in accordance with the following claims and their legal equivalents.

What is claimed is:

1. A method for displaying data gathered from a subject during a cardiopulmonary exercise test and computed relationships based on that data, comprising the steps of plotting, on a first graph having an x-axis, a first y-axis and a second y-axis, $\dot{V}O_2$ on the x-axis, heart rate on the first y-axis, and calculated stroke volume on the second y-axis using a computer;

displaying the first graph on a display;

plotting, on a second graph having an x-axis, a first y-axis and a second y-axis, $\dot{V}CO_2$ on the x-axis, $\dot{V}E$ on the first y-axis, and $SaO_2$ on the second y-axis using a computer;

displaying the second graph on a display;

plotting, on a third graph having an x-axis, a first y-axis and a second y-axis, $\dot{V}O_2$ on the x-axis, $\dot{V}CO_2$ on the first y-axis, and ratios $\dot{V}/\dot{V}CO_2$ and $\dot{V}E/\dot{V}O_2$ on the second y-axis using a computer;

displaying the third graph on a display;

plotting, on a fourth graph having an x-axis, a first y-axis and a second y-axis, time on the x-axis, heart rate on the first y-axis and $\dot{V}O_2$ on the second y-axis by using a computer; and displaying the fourth graph on a display.

2. The method of claim 1, wherein the first graph, the second graph, the third graph, and the fourth graph may be displayed in any order.

3. The method of claim 1, further comprising the step after the displaying the first graph step of printing the first graph; the step after the displaying the second graph step of printing the second graph; the step after the displaying the third graph step of printing the third graph; and the step after the displaying the fourth graph step of printing the fourth graph.

4. The method of claim 1, wherein the displaying the first graph step is replaced by the step of printing the first graph; the displaying the second graph step is replaced by the step of printing the second graph; the displaying the third graph step is replaced by the step of printing the third graph; and the displaying the fourth graph step is replaced by the step of printing the fourth graph.

5. A method for displaying data gathered from a subject during a cardiopulmonary exercise test and computed relationships based on that data, comprising the steps of:

plotting, on a first graph having an x-axis, a first y-axis and a second y-axis, $\dot{V}O_2$ on the x-axis, heart rate on the first y-axis, and calculated stroke volume on the second y-axis by computer means;

displaying the first graph;

plotting, on a second graph having an x-axis, a first y-axis and a second y-axis, $\dot{V}CO_2$ on the x-axis, $\dot{V}E$ on the first y-axis, and $SaO_2$ on the second y-axis using a computer;

displaying the second graph;

plotting, on a third graph having an x-axis, a first y-axis and a second y-axis, $\dot{V}O_2$ on the x-axis, $\dot{V}CO_2$ on the first y-axis, and ratios $\dot{V}E/\dot{V}CO_2$ and $\dot{V}E/\dot{V}O_2$ on the second y-axis using a computer;

displaying the third graph;

plotting, on a fourth graph having an x-axis, a first y-axis and a second y-axis, time on the x-axis, heart rate on the first y-axis and $\dot{V}O_2$ on the second y-axis using a computer; and displaying the fourth graph.

6. The method of claim 5, wherein the displaying steps are performed in the order of displaying the first graph, displaying the second graph, displaying the third graph, and displaying the fourth graph.

7. The method of claim 5, further comprising the step of printing the first graph.

8. The method of claim 5, further comprising the step of printing the second graph.

9. The method of claim 5, further comprising the step of printing the third graph.

10. The method of claim 5, wherein the step of plotting, on a second graph having an x-axis, a first y-axis and a second y-axis, $\dot{V}CO_2$ on the x-axis, $\dot{V}E$ on the first y-axis, and $SaO_2$ on the second y-axis by computer means, further comprises the step of:

plotting a reference line representing a $\dot{V}E/\dot{V}CO_2$ ratio substantially equal to 34.

11. A method for displaying data gathered from a subject during a cardiopulmonary exercise test and computed relationships based on that data, comprising the steps of:

plotting, on a first graph having an x-axis, a first y-axis and a second y-axis, $\dot{V}O_2$ on the x-axis, heart rate on the first y-axis, and calculated stroke volume on the second y-axis using a computer;

printing the first graph;

plotting, on a second graph having an x-axis, a first y-axis and a second y-axis, $\dot{V}CO_2$ on the x-axis, $\dot{V}E$ on the first y-axis, and $SaO_2$ on the second y-axis using a computer;

printing the second graph;

plotting, on a third graph having an x-axis, a first y-axis and a second y-axis, $\dot{V}O_2$ on the x-axis, $\dot{V}CO_2$ on the first y-axis, and ratios $\dot{V}E/\dot{V}CO_2$ and $\dot{V}E/\dot{V}O_2$ on the second y-axis using a computer;

printing the third graph;

plotting, on a fourth graph having an x-axis, a first y-axis and a second y-axis, time on the x-axis, heart rate on the first y-axis and $\dot{V}O_2$ on the second y-axis using a computer; and printing the fourth graph.

* * * * *